United States Patent [19]

Dunshee et al.

[11] Patent Number: 4,462,224

[45] Date of Patent: Jul. 31, 1984

[54] INSTANT HOT OR COLD, REUSABLE COLD PACK

[75] Inventors: Wayne K. Dunshee, Maplewood; Robert W. H. Chang, Roseville, both of Minn.

[73] Assignee: Minnesota Mining and Manufacturing Company, St. Paul, Minn.

[21] Appl. No.: 512,642

[22] Filed: Jul. 11, 1983

[51] Int. Cl.³ ............................................. F25D 3/08
[52] U.S. Cl. ........................................ 62/530; 62/4; 206/219
[58] Field of Search ................. 206/219; 53/431, 440; 62/4, 530

[56] References Cited

U.S. PATENT DOCUMENTS

| | | | |
|---|---|---|---|
| 2,916,886 | 12/1959 | Robbins | 62/294 X |
| 3,074,544 | 1/1963 | Bollmeier et al. | 206/47 |
| 3,542,032 | 11/1970 | Spencer, Jr. | 62/530 X |
| 3,545,230 | 12/1970 | Morse | 62/530 |
| 3,756,389 | 9/1973 | Firth | 206/219 |
| 3,763,622 | 10/1973 | Stanley, Jr. | 53/431 |
| 3,804,077 | 4/1974 | Williams | 126/263 |
| 3,847,279 | 11/1974 | Montgomery | 206/219 |
| 3,874,504 | 4/1975 | Verakas | 206/219 |
| 3,891,138 | 6/1975 | Glas | 206/219 X |
| 3,950,158 | 4/1976 | Gossett | 206/219 |
| 4,402,402 | 9/1983 | Pike | 206/219 |

Primary Examiner—Lloyd L. King
Attorney, Agent, or Firm—Donald M. Sell; James A. Smith; Robert W. Hoke, II

[57] ABSTRACT

A three-compartment, instant hot or cold, reusable cold pack for transferring heat to or from an object. A first compartment contains a predetermined amount of a solvent comprised primarily of water. A second compartment contains a predetermined amount of a solute capable of essentially completely dissolving in the solvent. A third compartment contains a gelling agent capable of gelling with the solvent and solute solution and producing a gel that is relatively soft and moldable when frozen.

20 Claims, 7 Drawing Figures

INSTANT HOT OR COLD, REUSABLE COLD PACK

BACKGROUND

The present invention relates to hot and cold packs. More particularly, it relates to a three-compartment, instant hot or cold, reusable cold pack for transferring heat to or from an object.

One type of hot or cold pack typically includes a rupturable container having a first chemical therein. A second chemical is positioned adjacent the rupturable container with the rupturable container preventing contact between the two chemicals. Upon rupture, the first and second chemicals mix to liberate or absorb heat and thereby produce the desired heating or cooling effect. One such pack is disclosed in U.S. Pat. No. 3,763,622.

Another type of a thermal pack is disclosed in U.S. Pat. No. 3,874,504. In one embodiment, an outer pouch slidably receives a sealed intermediate pouch containing the separated, thermally-active ingredients. When the pack is squeezed, a membrane separating the ingredients is ruptured and the heating or cooling effect realized. In another embodiment, different ingredients are premixed in an envelope to form a gel. The gel pack is placed in a refrigerator to lower its temperature prior to application to an object to be cooled.

The prior art hot or cold packs have been one of these two types. They have either been designed to provide an instant heating or cooling effect upon the mixing of two or more chemicals, or they have relied upon an outside source of heating or cooling. The latter form of packs have typically been gel packs. They have been cooled in a refrigerator to achieve the desired effect.

One advantage of the gel packs over the instant packs is their flexibility or moldability even when frozen. This is known to facilitate their use on curved surfaces. U.S. Pat. No. 3,545,230 discloses a number of insoluble hydrophylic gels which are said to be useful in cold packs. Packs made from the gels disclosed are said to be moldable even when frozen to conform to various geometric shapes. The packs are used by first freezing them and then applying them to the area to be cooled.

One such gel pack is marketed by Minnesota Mining and Manufacturing Company, 3M Center, St. Paul, Minn. 55144, under the trademark "COLD COMFORT". It is comprised of 70 weight percent water, 25 weight percent propylene glycol and 5 weight percent hydroxypropyl methylcellulose, type K15MDGS, as purchased from Dow Chemical Company, Midland, Mich. 48640 under the trademark "METHOCEL". The gel is made by first wetting the hydroxypropyl methylcellulose with the propylene glycol. The water is next added to form the finished gel.

U.S. Pat. No. 3,804,077 discloses an instant hot or cold pack which also forms a gel. The pack includes a first sealed compartment containing particles of a first material such as calcium chloride or ammonium nitrate. Particles of a suitable material such as a starch are mixed with the particles of the first material in the first compartment. The first compartment is disposed within a sealed second compartment containing a second material such as water and having rupturable properties. When the second compartment is ruptured, the materials in the two compartments are said to become mixed. The ammonium nitrate in the first compartment reacts endothermally with the water in the second compartment. The starch is said to form a gel and impede the movements of the materials in the pack. The inclusion of the starch in the pack is believed to be disadvantageous to the chemical reaction between the materials in the pack since it slows the rate at which the chemical reaction occurs and thus reduces the ultimate temperature change achievable. The starch is said to be advantageous since it is said to be compatible with the other materials in the pack and does not react chemically with any of these other materials in the pack to prevent these materials from reacting chemically with each other to produce the cooling effect. If it were frozen, it is believed the pack would be hard and inflexible.

The prior instant hot and cold packs have been able to provide heating and cooling effects at ambient temperatures, but they have been inadequate when frozen due to their hardness and inflexibility. Reusable gel packs have been soft and moldable when frozen, but they have been useless without the accessibility of a refrigerator to create the cooling effect. Never before have the advantages of the two types of packs been combined.

SUMMARY OF THE INVENTION

The thermal pack of the present invention overcomes the disadvantages of the prior packs by combining the advantages of an instant hot or cold pack with the advantages of a reusable cold pack.

According to the invention, there is provided a three-compartment, instant hot or cold, reusable cold pack for transferring heat to or from an object. A first compartment contains a predetermined amount of a solvent comprised primarily of water. A second compartment contains a predetermined amount of a particulate solute capable of essentially completely dissolving in the solvent whereby a predetermined amount of heat is liberated or absorbed. The two compartments are associated whereby the solute can be dissolved in the solvent. A third compartment contains a predetermined amount of a gelling agent capable of gelling with the solvent and solute solution at ambient temperature. The gel that is produced is relatively soft and moldable when cooled to temperatures at least as low as $-18°$ C. The third compartment is associated with the first compartment and the second compartment whereby the gelling agent can be gelled with the solvent and solute solution.

Mixing the contents of the first compartment and the second compartment provides an instant heating or cooling effect as in an instant hot or cold pack. Once the solution has returned to ambient temperature, the contents of the third compartment can be mixed with the contents of the first and second compartments to produce a gel. The characteristics of the gel are such that it will remain relatively soft and moldable when cooled to temperatures typically attainable in a refrigerator. Hence, the pack of the present invention is reusable as a gel pack.

BRIEF DESCRIPTION OF THE DRAWINGS

Other advantages of the invention will become apparent from the following drawings wherein like numerals refer to like parts, the accompanying description and the appended claims.

DETAILED DESCRIPTION

Figure 1:
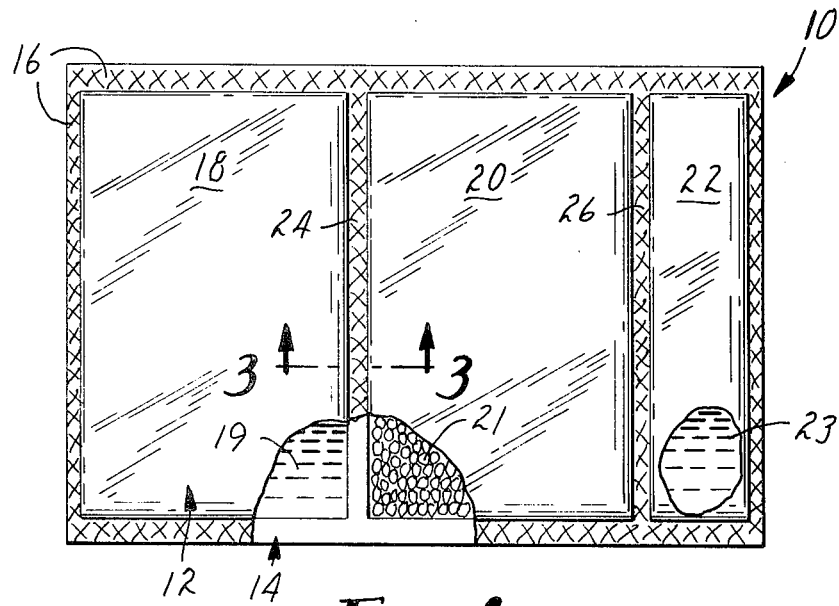
FIG. 1 is a top view of a three-compartment, instant hot or cold, reusable cold pack of the present invention with portions broken away.
Figure 2:
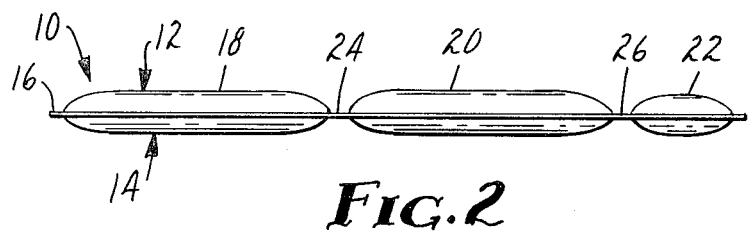
FIG. 2 is a side view of the pack of FIG. 1.
Figure 3:
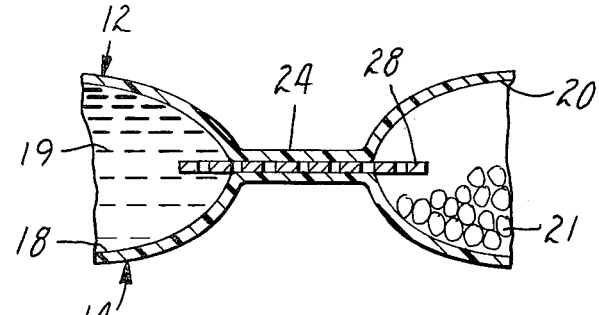
FIG. 3 is a greatly enlarged, fragmentary, cross-sectional view taken along the line 3—3 of FIG. 1.

Referring generally to FIGS. 1-3 and more particularly to FIG. 1, a three-compartment, instant hot or cold, reusable cold pack 10 of the present invention is shown. The pack 10 comprises a pair of rectangular sheets 12 and 14 of relatively strong and tough flexible material. One such material is "Scotchpak" brand heat sealable polyester film, type ET-29905, caliper 4.0 mil, part number 78-8041-9165-4, available from Minnesota Mining and Manufacturing Company, 3M Center, St. Paul, Minn. 55144. Sheets 12 and 14 are peripherally sealed to each other by a mechanically strong heat seal 16.

The pack 10 is separated into three compartments 18, 20 and 22 by predictably rupturable seams 24 and 26 joining sheets 12 and 14. The seams 24 and 26 extend transversely across the sheets 12 and 14 and through the peripheral heat seal 16 at opposite edges of the pack 10. The seams 24 and 26 must be sufficiently strong to maintain seals between the compartments 18, 20 and 22 during all normal handling. At the same time, the seams 24 and 26 must be substantially less resistant to rupture than the heat seal 16 and the sheets 12 and 14.

The rupture of the seam 24 is accomplished by gripping the sheets 12 and 14 in the middle of the compartment 18 and rapidly pulling or jerking the sheets 12 and 14 apart. Alternatively, the seam 24 can be ruptured by squeezing or kneading the compartment 18. Similarly, the sheets 12 and 14 are pulled apart in the middle of the compartment 22 to rupture the seam 26, or the compartment 22 can be ruptured by squeezing or kneading.

The reduced resistance to rupture is imparted to the seams 24 and 26 by a porous fibrous web 28 as shown in FIG. 3. The seams 24 and 26 are identical in construction. The construction of the seam 24 is shown in FIG. 3. The web 28 is made of open tissue-like paper or of non-woven polyester mat as further described in U.S. Pat. No. 3,074,544 which is incorporated by reference. The web 28 is interposed between the sheets 12 and 14. The web 28 preferably has approximately 50% through openings and does not chemically or mechanically bond well to one of the sheets 12 and 14. The sheets 12 and 14 are heat sealed together through the openings in the web 28. Hence, the seams 24 and 26 are actually a series of fused islands through which joinder of the sheets 12 and 14 is effected. As a result, the seams 24 and 26 are comparatively weaker than the seam 16 and the sheets 12 and 14.

The pack 10 is constructed by first forming rupturable seams 24 and 26 in the manner already described. Next, three sides of the peripheral heat seal 16 are formed as described. The fourth side, one of the longitudinal, common edges of the sheets 12 and 14, is left open to allow introduction of the reactive chemicals to be described. After introduction of a predetermined amount of each of the chemicals, the fourth side is sealed to form the hermetically sealed cold pack 10.

Figure 4:
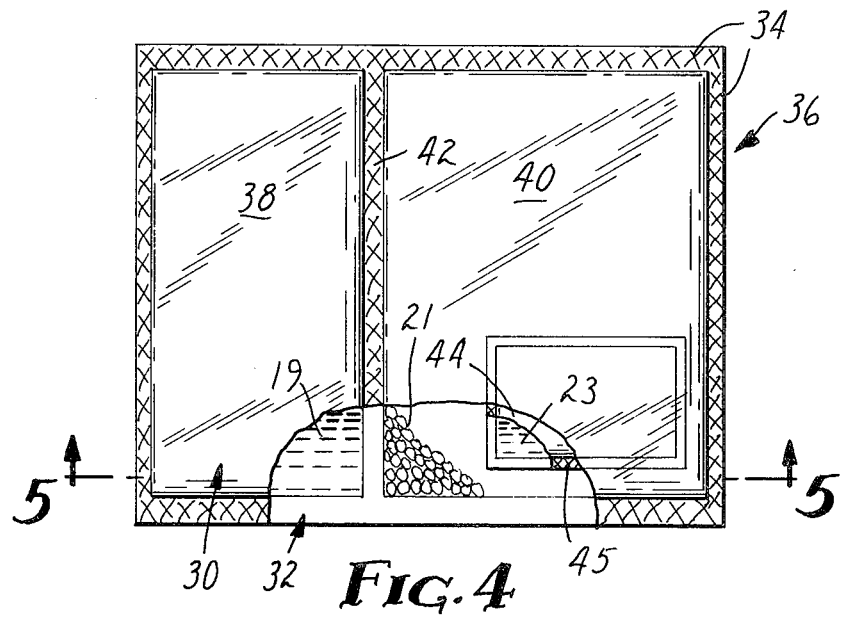
FIG. 4 is a top view of an alternative embodiment of a three-compartment, instant hot or cold, reusable cold pack of the present invention with portions broken away.
Figure 5:
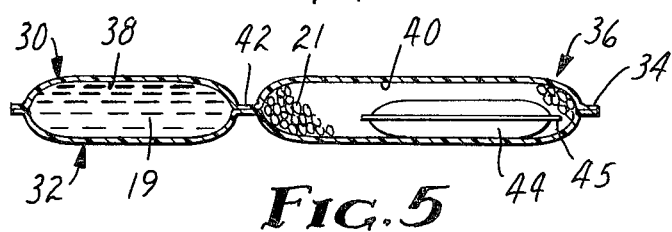
FIG. 5 is a cross-sectional view taken along the line 5—5 of FIG. 4.

Alternative, three-compartment, instant hot or cold, reusable cold pack constructions are illustrated in FIGS. 4-7. In FIGS. 4 and 5, a pair of rectangular sheets 30 and 32 of material such as that of sheets 12 and 14 are peripherally sealed to each other by a mechanically strong heat seal 34. The pack 36 is separated into two compartments 38 and 40 by a predictably rupturable seam 42 joining the sheets 30 and 32. The seam 42 is of a construction and exhibits rupture characteristics such as that of the seams 24 and 26.

Within the compartment 40 is a rupturable or water soluble compartment 44. If the compartment 44 is made rupturable, at least a portion of its peripheral seam 45 is constructed such as that of the seams 24 and 26, and the seam 45 is similarly ruptured. If the compartment 44 is water soluble, a number of satisfactory materials may be used. For example, one suitable cold water soluble polyvinyl alcohol film is available from the Mono-Sol Division of Chris Craft Industries, Inc., 407 County Line Road, Gary, Ind. 46403. It is denoted by number 7-0015-3.

Figure 6:
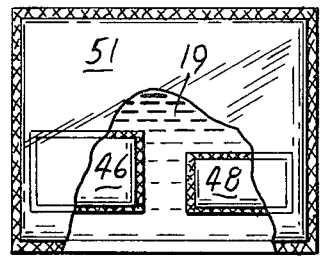
FIG. 6 is a top view of a second alternative embodiment of a three-compartment, instant hot or cold, reusable cold pack of the present invention with portions broken away.

Another alternative embodiment is shown in FIG. 6. It includes a pair of rupturable compartments 46 and 48 within a heat-sealed outer compartment 51. The compartments 46 and 48 are formed such as that of compartment 44. The outer compartment 51 is comprised of peripherally heat-sealed materials such as that used for packs 10 and 36.

Figure 7:
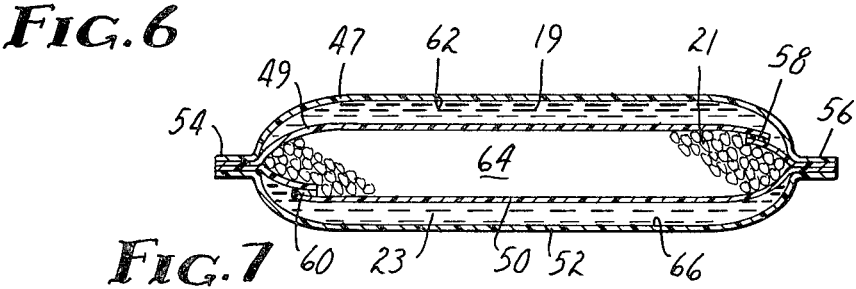
FIG. 7 is a cross-sectional view of a third alternative embodiment of a three-compartment, instant hot or cold, reusable cold pack of the present invention.

Yet another alternative embodiment is shown in FIG. 7. It again comprises three compartments formed from a combination of heat sealed and rupturably seamed sheets 47, 49, 50 and 52. The sheets 47, 49, 50 and 52 are sealed at heat seals 54 and 56. The sheets 49 and 50 include rupturable seams 58 and 60, respectively, to form three compartments 62, 64 and 66. The seams 58 and 60 are ruptured in the manner already described by gripping and pulling apart the sheets 47, 49, 50 and 52 near heat seals 56 and 54, respectively. The sheets 47, 49, 50 and 52 are pulled apart near the heat seals 54 and 56 nearest the rupturable seams 60 and 58, respectively, to be ruptured.

The commonality of the above-described, alternative packs is the inclusion of three compartments. In each embodiment, the three compartments separate the reactants to be described. Generally, upon the mixing of the contents of two compartments, heat is liberated or absorbed and a heating or cooling effect immediately produced. Upon the mixing of the contents of the third compartment with the product of the mixture of the other two compartments, a gel is formed. The resultant gel is comparatively soft and moldable when cooled to temperatures generally attainable in normal household refrigerators, i.e., at least as low as $-18°$ C. The details of the contents of each of the three compartments, the order in which the compartments are mixed and the properties of the resultant gels will next be described in conjunction with FIG. 1.

In practice, the pack 10 can be made of any practical size and shape. The size of the compartments 18, 20 and 22 can be varied to accommodate the amount of chemicals deposited therein as well known in the art. Within each of the compartments is a predetermined amount of each of the chemicals. The amounts will be expressed as weight percentages.

The compartment 18 of the pack 10 is filled with a solvent 19 comprised primarily of water. The compartment 20 is filled with an amount of a water soluble solute 21 capable of exothermally or endothermally dissolving in the water. The solute 21 is added in particulate form in an amount capable of essentially completely dissolving in the solvent 19. Any more than that is a waste of the solute 21 since it will not dissolve in the solvent 19. Solutes believed to be suitable are listed in Table I. In the case of each solute listed, solute weighing between 65% and 135% of the weight of an essentially pure water solvent can be essentially completely dissolved in the water solvent. Preferably, the solute and solvent are added in equal weight amounts. The preferred exothermic solute is calcium chloride. The preferred endothermic solute is ammonium nitrate.

TABLE I

| Exothermic Solutes | Endothermic Solutes |
| --- | --- |
| $AlCl_3 \cdot 6H_2O$ | $NH_4NO_3$ |
| $CaBr_2$ | $NH_4Br$ |
| $CaCl_2$ | $NH_4I$ |
| $CaCl_2 \cdot H_2O$ | $KCl$ |
| $FeCl_2$ | $SnCl_2 \cdot 2H_2O$ |
| $MgBr_2$ | $CO(NH_2)_2$ |
| $MgCl_2$ | $CoCl_2 \cdot 6H_2O$ |
| $MnCl_2$ | $Ni(NO_3)_2 \cdot 6H_2O$ |
| $Mn(NO_3)_2$ | |
| $NiCl_2$ | |
| $ZnCl_2$ | |

If the pack 36 of FIG. 4 is used rather than the pack 10 of FIG. 1, the compartment 40 is filled with the solute 21, the compartment 38 is filled with the solvent 19 and the compartment 44 is filled with a gelling agent 23. In this way, the water soluble compartment 44 is kept away from the solvent 19 comprised primarily of water, until seam 42 is ruptured.

Upon the rupture of the seam 24, the solvent and the solute are mixed, and a predetermined amount of heat is given off or absorbed. The amount of heat that is evolved or absorbed is a function of the amount and composition of the solute 21 that is dissolved. It can be determined by reference to standard references as well known in the art.

After the contents of the combined compartments 18 and 20 have returned to ambient temperatures and the therapeutic heating or cooling effect exhausted, the pack 10 may be converted to a reusable gel pack by rupturing seam 26 and releasing the contents of the compartment 22 to mix with the contents of the remainder of the pack 10. The embodiments of FIGS. 6 and 7 are similarly ruptured. In the embodiment of FIGS. 4 and 5, the conversion to a reusable gel pack is automatically made by the dissolution of the compartment 44 when the compartment 44 is made water soluble and is exposed to the water solution.

The contents of the compartment 22 of the pack 10 of FIG. 1 generally comprise a gelling agent 23. Gelling agents believed to be suitable are listed in TABLE II. They may be divided into natural gum polymers and cellulosics or cellulose derivatives. In each instance, the gelling agent preferably comprises 3 to 6 weight percent of the total weight of the chemicals within the compartments 18, 20 and 22.

TABLE II

Gelling Agents

Natural Gum Polymers
Guar Gum
Gum Tragacanth
Locust Bean Gum
Xanthan Gum
Cellulosics
Hydroxypropyl Methylcellulose
Liporamnosan Brand Polyethylene Glycol (12) Glucopiranose Copolymer
Idroramnosan Brand Polyethylene Glycol (8) Glucopiranose Copolymer
Hydroxyethyl Cellulose
SGP Brand Absorbent Polymer Hydroxypropyl methylcellulose is generally available in a finely divided, particulate form. If it is used as the gelling agent, it must be thoroughly prewetted. Suitable wetting agents include propylene glycol, ethylene glycol, methanol or ethanol. The glycol or alcohol is used to thoroughly wet out the hydroxypropyl methylcellulose prior to mixing with the water solvent. By "wetting out" it is meant the surface of the hydroxypropyl methylcellulose is prevented from being repellant to the solvent and solute mixture within the combined compartments 18 and 20. Glycol or alcohol weighing between 10 and 25 weight percent of the total weight of the chemicals within the compartments 18, 20 and 22 will thoroughly wet out the hydroxypropyl methylcellulose. A suitable hydroxypropyl methylcellulose is available from Dow Chemical Company, Midland, Mich. 48640. It is type F4M. Another suitable hydroxypropyl methylcellulose is type K15MDGS. It, too, is available from Dow Chemical Company. Other hydroxypropyl methylcelluloses are believed to produce a suitable gel when prepared according to the present invention.

Liporamnosan Brand Polyethylene Glycol (12) Glucopiranose Copolymer and Idroramnosan Brand Polyethylene Glycol (8) Glucopiranose Copolymer are available from Tri-K Industries. SGP Brand Absorbent Polymer is a hydrolyzed starch-polyacrylonitrile graft copolymer available from Grain Processing Corporation, Muscatine, Iowa 52761.

In the preferred embodiment, hydroxypropyl methylcellulose and propylene glycol comprise 4 weight percent and 12 weight percent, respectively, of the total weight of a water, ammonium nitrate, hydropypropyl methylcellulose and propylene glycol cold pack. The water and the ammonium nitrate each make up 42 percent of the remaining weight of the chemicals.

Referring again to the pack 10 shown in FIG. 1, upon rupture of the seam 26, the contents of the compartment 22 of the pack 10 are mixed with the solution of the compartments 18 and 20 to form a gel. The gel is formed from a lesser percent water than known in the prior art. Yet, it exhibits comparable thermal properties and a viscosity at room temperatures of greater than 100,000 centipoise. This is particularly surprising in view of the amount of solute included within the mixture. Addition of a salt such as ammonium nitrate or calcium chloride, for example, to a gel is known to be one way to break a gel. Instead, the present invention produces a gel having a viscosity greater than 100,000 centipoise at ambient and exhibiting comparable thermal properties and with only a fraction of the water used in the prior gel packs.

Having a viscosity of at least 100,000 centipoise is important. Gels exhibiting lower viscosities at room temperatures tend to "saddle bag" or fall away from the patient. The higher viscosity gels tend to stay in place better and deliver more of the therapeutic cooling effect to the area to be treated.

Representative examples of the gels prepared according to the present invention are listed in TABLE III. The examples are representative only and are not intended to be limiting or exhaustive. In each instance a total of about 300 grams of chemicals were mixed, and the resultant gel sealed in a 10.2 cm by 25.4 cm pouch made of two sheets of low density polyethylene sealed at the edges. The times listed are the times required for the temperature of the individual gel packs to rise from −23° C. to +10° C. at an ambient of 24° C. 10° C. is the temperature at which the therapeutic effects of cold packs are believed to be substantially exhausted. The temperatures were determined using a constant temperature mat and a "J" thermocouple connected to a Moseley Autograf Model 680 Chart Recorder. The recorder was set at 5 millivolts and recorded sensed temperatures between −20° C. and +80° C. The 0° C. point was maintained by immersing the thermocouple in an ice and water bath.

The time required for the gel of each example to rise in temperature from −23° C. to +10° C. was determined by placing the connected thermocouple directly on the constant-temperature mat. The pouch, containing the gel, was next laid on top of the mat much as it would be applied to a body to be cooled. The thermocouple was located generally in the center of the pouch as viewed from above. Care was taken to insure contact between the pouch and the thermocouple and between the thermocouple and the underlying, constant-temperature mat. The temperature measured, then, was the temperature at the interface between the pouch and the mat.

The constant temperature mat used measured 15 cm by 39 cm overall. It was made of two sheets of ethylene vinyl acetate sealed at the edges. The mat included five transverse baffles spaced at 6.5 cm intervals along the 39 cm length of the mat. Alternate baffles were connected to opposite 39 cm edges of the mat. Each baffle was about 10 cm long, forcing a fluid circulated through the mat to follow a circuitous path. The fluid entered in a corner of the mat adjacent the first baffle, and it exited in a corner adjacent the fifth baffle. The two corners had a common 39 cm edge.

The fluid used was a 50 weight percent propylene glycol and 50 weight percent water solution. It was maintained at 24° C. by circulation from the mat to a one gallon reservoir and back to the mat. The one gallon reservoir was maintained by a heater at a constant 24° C.

Each example included in the TABLE III was prepared by first thoroughly wetting the gelling agent with the wetting agent. Next, the solute was completely dissolved in the solvent. The resultant solution was added to the wetted gelling agent, and the combination vigorously mixed into a consistent gel.

TABLE III

| Gel Formulation | | | | | |
|---|---|---|---|---|---|
| Water Solvent | Solute | Gelling Agent | Wetting Agent | −23° C. to 10° C. Time | Ambient Viscosity |
| 35 wt. % | 35 wt. % $NH_4NO_3$ | 5 wt. % F4M Methocel | 25 wt. % propylene glycol | 15 minutes | >1,000,000 centipoise |
| 42.5 wt. % | 42.5 wt. % $NH_4NO_3$ | 5 wt. % F4M Methocel | 10 wt. % propylene glycol | 31.0 minutes | 273,000 centipoise |
| 41.83 wt. % | 41.83 wt. % $NH_4NO_3$ | 4 wt. % F4M Methocel | 12.33 wt. % propylene glycol | 29.0 minutes | >1,000,000 centipoise |
| 40.5 wt. % | 40.5 wt. % $NH_4NO_3$ | 4 wt. % F4M Methocel | 15 wt. % propylene glycol | 25.6 minutes | 563,000 centipoise |
| 40 wt. % | 40 wt. % $NH_4NO_3$ | 5 wt. % F4M Methocel | 15 wt. % propylene glycol | 21 minutes | >1,000,000 centipoise |
| 37.5 wt. % | 37.5 wt. % $NH_4NO_3$ | 5 wt. % F4M Methocel | 20 wt. % propylene glycol | 13.5 minutes | >1,000,000 centipoise |
| 40 wt. % | 40 wt. % $NH_4NO_3$ | 5 wt. % F4M Methocel | 15 wt. % ethanol | 17 minutes | >1,000,000 centipoise |
| 40 wt. % | 40 wt. % $NH_4NO_3$ | 5 wt. % SGP | 15 wt. % propylene glycol | 19.0 minutes | 183,000 centipoise |
| 40 wt. % | 40 wt. % $NH_4NO_3$ | 5 wt. % gum tragacanth | 15 wt. % propylene glycol | 16.5 minutes | 170,000 centipoise |
| 40 wt. % | 40 wt. % $NH_4NO_3$ | 5 wt. % guar gum | 15 wt. % propylene glycol | 18.3 minutes | >1,000,000 centipoise |
| 43.75 wt. % | 31.25 wt. % $NH_4NO_3$ | 5 wt. % F4M Methocel | 20 wt. % propylene glycol | 11 minutes | >1,000,000 centipoise |
| 51.33 wt. % | 28.66 wt. % $NH_4NO_3$ | 5 wt. % F4M Methocel | 15 wt. % porpylene glycol | 19.5 minutes | >1,000,000 centipoise |
| 40 wt. % | 28 wt. % $CO(NH_2)_2$ and 12 wt. % KCl | 5 wt. % F4M Methocel | 15 wt. % propylene glycol | 11 minutes | >1,000,000 centipoise |
| 37.5 wt. % | 37.5 wt. % $NH_4NO_3$ | 5 wt. % F4M Methocel | 20 wt. % methanol | 11.5 minutes | 780,200 centipoise |

By way of comparison, the Cold Comfort brand gel pack described earlier was tested in the same manner. It warmed from −23° C. to +10° C. in 26 minutes and exhibited a viscosity at ambient temperatures greater than 1,000,000 centipoise. Hence, the gels of the present invention produced similar cooling effects under the test conditions with comparatively less water by weight and in the presence of significant amounts of solute materials.

Various modifications and changes may be made by one skilled in the art and without departing from the spirit of the invention as expressed in the accompanying claims. Hence, all matter shown and described is to be interpreted as illustrative and not in a limiting sense.

What is claimed is:

1. An instant hot or cold pack for transferring heat to or from an object adapted to be reuseable as a cold pack comprising:
   a. a first compartment containing a predetermined amount of a solvent comprised primarily of water;
   b. a second compartment containing a predetermined amount of a particulate solute capable of essentially completely dissolving in the solvent whereby a predetermined amount of heat is liberated or absorbed;
   c. means for mixing the contents of the first compartment and the second compartment at the time of use whereby the solute can be dissolved in the solvent;
   d. a third compartment containing a predetermined amount of a gelling agent capable of gelling with the solvent and solute solution at ambient temperature and producing a gel that is relatively soft and moldable when cooled to temperatures at least as low as $-18°$ C.; and
   e. means for mixing the contents of the third compartment with the previously-mixed contents of the first compartment and the second compartment whereby the gelling agent can be gelled with the solvent and the solute solution.

2. The pack recited in claim 1 further comprising a predetermined amount of a wetting agent contained within the third compartment and capable of thoroughly wetting out the gelling agent at ambient temperatures.

3. The pack recited in claim 2 wherein the gelling agent comprises 3-6 percent of the combined total weight of the solvent, the solute and the gelling agent.

4. The pack recited in claim 3 wherein the gel has a viscosity at ambient temperatures greater than 100,000 centipoise.

5. The pack recited in claim 4 wherein the gel warms from $-23°$ C. to $+10°$ C. in 10-30 minutes at ambient temperatures when about 300 grams of the gel is sealed in a 10.2 cm by 25.4 cm pouch and placed on a constant-temperature mat maintained at 24° C.

6. The pack recited in claim 5 wherein the amount of the solute comprises 65-135 weight percent of the weight of the solvent.

7. The pack recited in claim 6 wherein the solute is comprised primarily of calcium chloride or ammonium nitrate.

8. The pack recited in claim 7 wherein the gelling agent is hydroxypropyl methylcellulose, a natural gum polymer or a cellulosic.

9. The pack recited in claim 8 wherein the wetting agent comprises 10-25 percent of the combined total weight of the solvent, the solute and the gelling agent.

10. The pack recited in claim 9 wherein the wetting agent is propylene glycol, ethylene glycol, methanol or ethanol.

11. An instant hot or cold pack for transferring heat to or from an object adapted to be reuseable as a cold pack comprising:
   a. two generally rectangularly-shaped sheets of heat sealable material, each sheet having upper and lower major surfaces bound together by two longitudinal and two transverse edge surfaces, peripherally heat sealed adjacent the edge surfaces and defining a generally rectangularly shaped, hermetically sealed pack;
   b. two generally parallel, spaced apart, rupturable seams generally normal to and extending from one longitudinal heat seal to the other longitudinal heat seal and defining a first, a second and a third compartments within the pack;
   c. a predetermined amount of a solvent comprised primarily of water contained within the first compartment;
   d. a predetermined amount of a particulate solute capable of essentially completely dissolving in the solvent contained within the second compartment; and
   e. a predetermined amount of a gelling agent, capable of gelling with a solution of the solvent and the solute and producing a gel that is relatively soft and moldable when cooled to temperatures at least as low as $-18°$ C., contained within the third compartment.

12. The pack recited in claim 11 further comprising a predetermined amount of a wetting agent contained within the third compartment and capable of thoroughly wetting out the gelling agent at ambient temperatures.

13. The pack recited in claim 12 wherein the gelling agent comprises 3-6 percent of the combined total weight of the solvent, the solute and the gelling agent.

14. The pack recited in claim 13 wherein the gel has a viscosity at ambient temperatures greater than 100,000 centipoise.

15. The pack recited in claim 14 wherein the gel warms from $-23°$ C. to $+10°$ C. in 10-30 minutes at ambient temperatures when about 300 grams of the gel is sealed in a 10.2 cm by 25.4 cm pouch and placed on a constant-temperature mat maintained at 24° C.

16. The pack recited in claim 15 wherein the amount of the solute comprises 65-135 weight percent of the weight of the solvent.

17. The pack recited in claim 16 wherein the solute is comprised primarily of calcium chloride or ammonium nitrate.

18. The pack recited in claim 17 wherein the gelling agent is hydroxypropyl methylcellulose, a natural gum polymer or a cellulosic.

19. The pack recited in claim 18 wherein the wetting agent comprises 10-25 percent of the combined total weight of the solvent, the solute and the gelling agent.

20. The pack recited in claim 19 wherein the wetting agent is propylene glycol, ethylene glycol, methanol or ethanol.

* * * * *